US00PP09789P

United States Patent [19]

Kramer

[11] Patent Number: Plant 9,789

[45] Date of Patent: Jan. 28, 1997

[54] HEATHER 'MELANIE'

[76] Inventor: Kurt Kramer, Edanmer Strase 26, 26188 Edewecht, Germany

[21] Appl. No.: 505,814

[22] Filed: Jul. 21, 1995

[51] Int. Cl.[6] ..... A01H 5/00

[52] U.S. Cl. ..... Plt./54.1

[58] Field of Search ..... Plt./54.1

[56] References Cited

PUBLICATIONS

Bud-Flowering Heathers, article by David McClintock, published in The Garden, Nov. 1994, p. 543 (Table of Contents attached).

*Primary Examiner*—James R. Feyrer

*Attorney, Agent, or Firm*—Chernoff, Vilhauer, McClung & Stenzel

[57] ABSTRACT

A new and distinct variety of *Calluna vulgaris* heather has white flowers which remain as unopened buds through their entire cycle from fall through early spring.

3 Drawing Sheets

BACKGROUND AND SUMMARY OF THE INVENTION

The present invention relates to a new and distinct variety of bud flowering *Calluna vulgaris*. This new variety was developed by Kurt Kramer at Edewecht, Germany from a cross between two unpatented *Calluna vulgaris* developed by Mr. Kramer; No. 83-15-1 (seed parent) and 83-15-2 (pollen parent). The numbers were assigned to these varieties by Mr. Kramer. Both parents are marketed in Germany and both are *Calluna vulgaris* or "bud flowering" heathers. Cross pollination between bud flowering heathers is difficult since the flowers never open, but Mr. Kramer was able to do so to create the subject variety and its sister varieties Alexandra and Romina. The resulting seeds were planted in 1986. From these seedlings 19 plants were selected and planted in a field. The subject plant of this disclosure was subsequently selected from these 19 seedlings. The subject variety has been asexually reproduced at Edewecht, Germany from cuttings and subsequent generations have been true to form in all respects.

The subject variety produces buds in the fall having a unique white color. The buds do not open into flowers but remain in the bud stage through the winter, approximately six months, from October to March, in Edewecht, Germany. The subject variety has a dense upright globular shape with protruding flower shoots which are heavily budded. The overall height of the plant at maturity, is approximately 24 inches with 6–8 inch shoots.

The closest varieties known to the applicant that have been publicly disclosed in Europe are Alexandra, a purple bud flowering Heather also developed by Kurt Kramer, and the subject of U.S. plant patent application Ser. No. 08/459,510, filed Jun. 2, 1995. To the best of applicant's knowledge, Alexandra has not been brought into the United States.

DETAILED DESCRIPION OF THE NEW VARIETY

Figure 1:
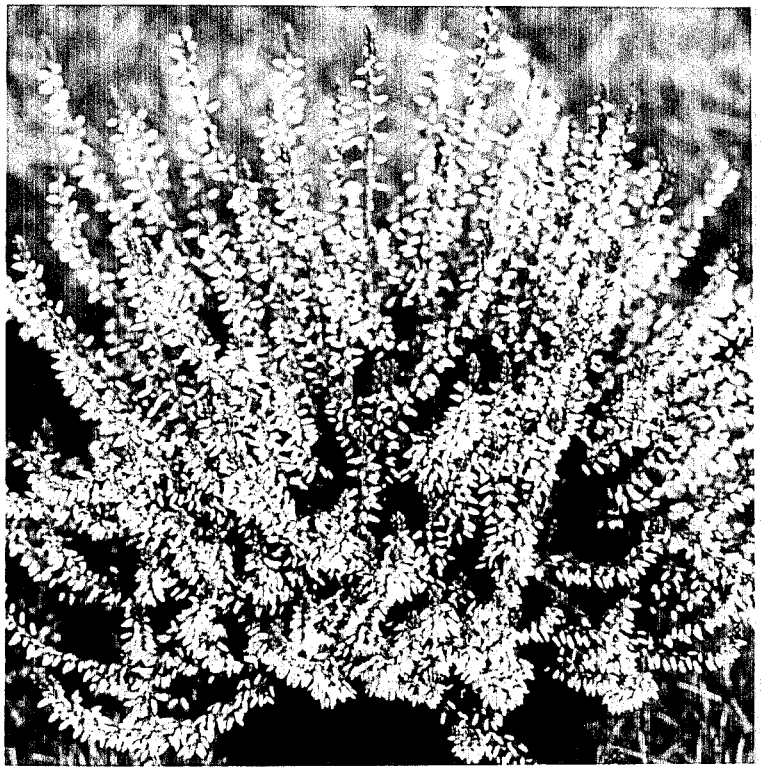
FIG. 1 shows the subject variety planted in the ground in Edewecht, Germany in October showing the color of the bud and shape of the plant.
Figure 2:
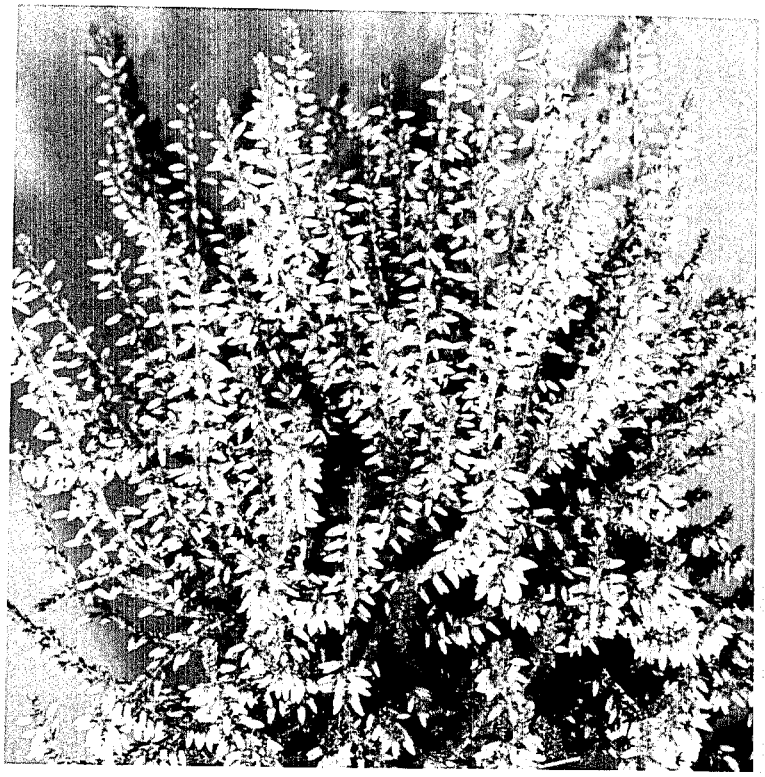
FIG. 2 shows the subject variety in a pot at about the same time period.
Figure 3:
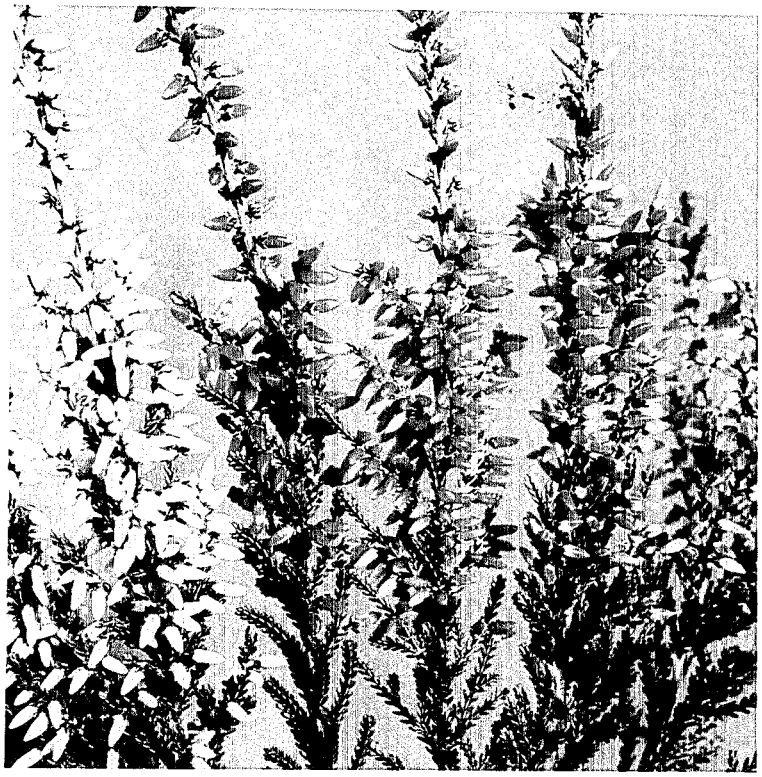
FIG. 3 shows the shoots and buds of the subject variety.

The following is a detailed description of the new variety of Heather plant based upon observations of plants grown at Edewecht, Germany. Color references are to The Royal Horticultural Society Color Chart except where general color terms of ordinary dictionary significance are used.

PLANT

Botanical description: *Calluna vulgaris* (L.) Hull.

Common description: Broom Heather.

Form: Woody Shrub, perennial, evergreen.

Shape: Low, strongly basally branching shrub with very dense branching; habit is generally mounded with a profusion of weakly terminally dominant branches below flower spike which occur at the apices of main branches.

Height: Approximately 24 inches, including flower spikes, at maturity.

Main stem:

*Length.*—Approximately 24 inches, including flower spikes, at maturity.

*Color.*—Yellow-green — 151A in April, tends to get lighter through the growing season.

*Branching.*—Heavily branched until the spike. The spike has a plurality of auxiliary verticils of clusters of 2 to 4 buds outwardly radiating from the apices of oppositely placed, short branches arising out of leaf axils of bilobularly attached leaves, with stem pairs on a plane 90° to the plane of adjacent pairs.

Growth: Approximately 8 inches per year, very vigorous; ultimate height without spike is approximately 16 inches.

Foliage: Leaves are oppossitely placed, scale-like and bractiolate, sessile, and occur in 4 rows on stems which are essentially square in cross-section.

*Leaf length.*—1.5–6.0 mm.

*Leaf width.*—0.8–1.5 mm.

*Leaf color.*—Color of plant ends in spring — light green 149D. Color of plant ends in winter — mid green 141A. Color of main plant in summer — yellow green 143A.

Flower spikes: Formed at the terminals of main branches, having a plurality of uniformly spaced auxiliary verticils with clusters of 2 to 4, or more, mature buds outwardly radiating from the apex of oppositely placed, short branches which arise out of leaf axils of bilobularly attached bractiolate leaves; stem pairs are on a plane 90 to the plane of adjacent pairs; length of spikes is normally about 6–8 inches, presenting a profusion of mature buds from base to the progressively bud-forming terminal; the number of buds formed is about average for the species.

Pruning: No pruning is equired except to maintain shape. Removal of spikes from the previous season will promote better growth of new spikes.

BUD

Color of bud at full development: White 155D. The bud does not open to a flower. It stays a bud during its season.

Budding period: 6 months — fall through early spring.

Bud diameter: Approximately ⅛ inch.

Bud length: Approximately ¼ inch.

Bud shape: Truncated Elliptic.

Inflorescence: The corolla and reproductive organs of the plant are identical to those of the species; corolla color — white 155D. There are 4 sepals which fads after the first frost. The plant does not produce seed because the style is covered by the sepals. Reproduction is by cuttings.

What is claimed is:

1. A new and distinct variety of Heather plant named *Calluna vulgaris* Melanie, substantially as herein shown and described, characterized particularly by its white flowers which remain as an unopened bud from fall through early spring.

* * * * *

UNITED STATES PATENT AND TRADEMARK OFFICE

CERTIFICATE OF CORRECTION

PATENT NO. : Plant 9,789

DATED : January 28, 1997

INVENTOR(S) : Kurt Kramer

It is certified that error appears in the above-indentified patent and that said Letters Patent is hereby corrected as shown below:

| | | | |
|---|---|---|---|
| Col. | 1, | Line 45 | After "variety" insert --along with the shoots and buds of the Alexandra variety--. |
| Col. | 2, | Line 19 | Delete "spike" and insert --spikes--. |
| Col. | 3, | Line 11 | Delete "equired" and insert --required--. |
| Col. | 4, | Line 7 | Delete "fads" and insert --fade--. |

Signed and Sealed this

Twenty-second Day of July, 1997

Bruce Lehman

*Attest:*

BRUCE LEHMAN

*Attesting Officer*

*Commissioner of Patents and Trademarks*